United States Patent [19]
Er et al.

[11] Patent Number: 5,891,179
[45] Date of Patent: Apr. 6, 1999

[54] METHOD AND APPARATUS FOR MONITORING AND DISPLAYING LEAD IMPEDANCE IN REAL-TIME FOR AN IMPLANTABLE MEDICAL DEVICE

[75] Inventors: Siew Bee Er, Newhall; Robert E. Smith, Jr., Bradbury, both of Calif.

[73] Assignee: Paceseter, Inc., Sylmar, Calif.

[21] Appl. No.: 974,438

[22] Filed: Nov. 20, 1997

[51] Int. Cl.$^6$ .............................. A61N 1/362; A61N 1/37
[52] U.S. Cl. ............................................................ 607/27
[58] Field of Search .................................. 607/26, 27, 32

[56] References Cited

U.S. PATENT DOCUMENTS

| | | |
|---|---|---|
| 4,899,750 | 2/1990 | Ekwall . |
| 5,425,373 | 6/1995 | Causey, III . |
| 5,431,691 | 7/1995 | Snell et al. . |
| 5,475,307 | 12/1995 | Silvian . |
| 5,549,646 | 8/1996 | Katz et al. . |
| 5,683,427 | 11/1997 | Ekwall . |
| 5,713,937 | 2/1998 | Nappholz et al. . |
| 5,755,742 | 5/1998 | Schuelke et al. . |

*Primary Examiner*—William E. Kamm
*Assistant Examiner*—Carl H. Layno

[57] ABSTRACT

A real-time impedance monitoring system is provided for use with an implantable medical device having an implantable electrical lead. The impedance monitoring system includes components for determining the electrical impedance of the lead as a function of time, with the determination being made substantially in real-time, and components for graphically displaying the electrical impedance of the lead as a function of time, with the display also being generating substantially in real-time. In one specific example described herein, the implantable medical device is a pacemaker and the impedance monitoring system is within an external programmer device separate from the pacemaker. The programmer device includes a computer display screen or a computer printout device for presenting real-time graphical displays of the lead impedance. The programmer may alternatively generate graphical displays of lead impedance as a function of time based upon pre-recorded data.

20 Claims, 6 Drawing Sheets

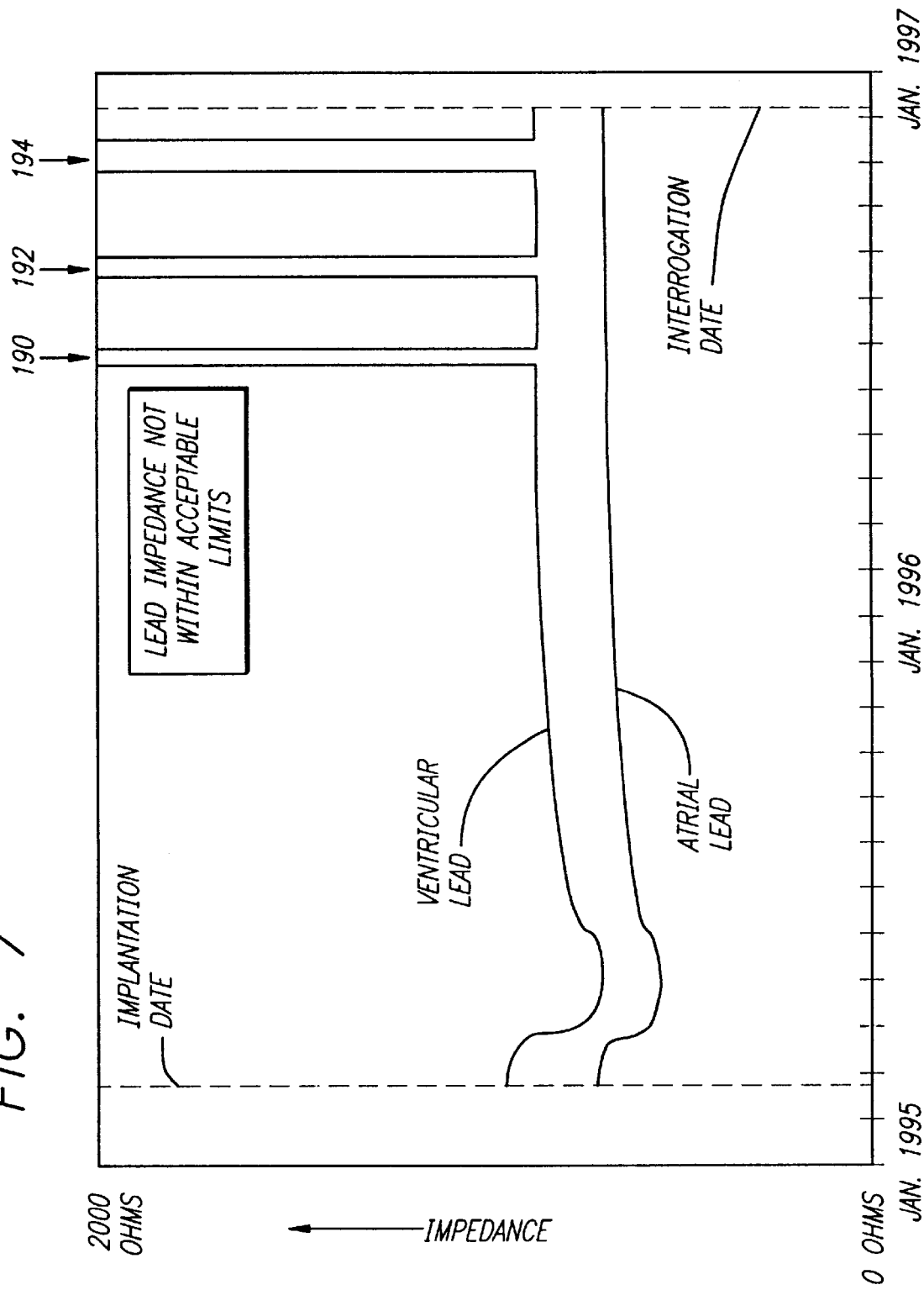

METHOD AND APPARATUS FOR MONITORING AND DISPLAYING LEAD IMPEDANCE IN REAL-TIME FOR AN IMPLANTABLE MEDICAL DEVICE

FIELD OF THE INVENTION

The invention generally relates to implantable medical devices and to external programmer devices used in connection therewith and in particular to methods and apparatus for detecting and processing the electrical impedance of one or more electrical leads of the implantable medical device.

BACKGROUND OF THE INVENTION

A wide range of implantable medical devices are provided for surgical implantation into humans or animals. One common example is the cardiac pacemaker. Another is the implantable cardioverter defibrillator (ICD). Other examples include devices for stimulating or sensing portions of the brain, spinal cord, muscles, bones, nerves, glands or other body organs or tissues.

Many such implantable medical devices include one or more electrical leads for conducting sensed electrical signals away from a particular part of the body such as the heart or for conducting stimulating electrical signals to the particular part of the body. In the case of a pacemaker, the sensed electrical signals are typically representative of P-waves and R-waves. The stimulating electrical signals are small pulses of electricity, on the order of micro-joules, for stimulating the heart in the event that the expected P-waves or R-waves are not detected. In the case of an ICD, the stimulating signals are typically 10 to 30 joule pulses of electricity provided to terminate tachycardia or fibrillation.

The electrical leads, for various reasons, may cease to function properly. For example, the electrical lead may suffer some minor damage during implantation that may affect the electrical insulation of the lead. This type of damage may not be initially detectable but may manifest itself after an extended period of time. In particular, stress imposed on the electrical lead as a result of the normal movements of the body may further damage the lead resulting in a complete or otherwise significant breakdown in the electrical insulation of the lead. In other cases, the lead itself may fracture. If either type of damage occurs, serious or even disastrous consequences may result. For example, in the case of a pacemaker or ICD electrical stimulation signals intended for the heart may be shunted to other parts of the body rendering the stimulation signals ineffective for pacing the heart or for terminating tachycardia or fibrillation.

Accordingly, various techniques have been developed for testing implanted electrical leads to detect lead faults such as lead fractures or complete breakdowns in insulation. To this end, many pacemakers now include circuitry for periodically or continuously testing the impedance of electrical leads connected to the pacemaker and any significant deviation from a range of acceptable impedance values is recorded within the pacemaker (subject to memory-space limitations) for subsequent downloading to an external monitoring device such as a pacemaker programmer. The downloaded data is analyzed by the external monitoring device to determine if an unexpected impedance value had been recorded by the pacemaker. Typically, the external monitoring device determines whether any of the recorded impedance values exceeds a predetermined upper threshold, such as 2000 ohms, or any falls below a predetermined lower threshold, such as 200 ohms. If the lead impedance exceeds the upper threshold, the lead is presumed to have fractured and must be replaced. If the impedance falls below the lower threshold, the insulation of the lead is presumed to have failed and the lead therefore also must be replaced. In either case, an audible warning signal or other simple notification is provided to the physician operating the external monitoring device. In other cases, the testing of the lead occurs while the pacemaker is in communication with the external monitoring device allowing such warning signals to be generated immediately. In still other cases, the pacemaker itself tests for unexpected impedance values and generates a warning signal within the patient by producing a high-pitched audible tone or by providing a mild, but noticeable electrical shock, to the patient.

Although the testing of electrical leads and the generation of simple warning signals upon the detection of an unexpected impedance value represents an improvement over systems which do not provide for lead testing, considerable room for improvement remains. In particular, with the generation of only a simple warning signal, the physician may not be provided with sufficient information to readily determine the exact nature and seriousness of the lead fault. The physician may not be able to determine easily, for example, whether the fault is a permanent fault or merely an intermittent one. If intermittent, the physician may not be able to determine easily whether the intermittent fault lasts only momentarily or for a longer period of time. As can be appreciated, further information regarding the exact nature of the lead fault may be required by the physician before he or she can determine the seriousness of the fault and, in particular, determine whether the lead must be replaced immediately or whether such action can be deferred at least temporarily. Moreover, further information regarding the exact nature of the fault may even be required before the physician can properly diagnose the patient. For example, a patient exhibiting an intermittent arrhythmia may have a faulty lead. If the lead fault is intermittent, the arrhythmia may be triggered by the absence of pacing signals during the intermittent faults. However, if the fault is permanent, the intermittent arrhythmia may have some other cause which may need to he further investigated.

Indeed, without further information regarding the exact nature of the fault, the physician may not even be able to determine easily whether the fault actually exists or whether the unexpected impedance values that have been detected are caused by some malfunction in either the pacemaker or the external monitoring device. For example, the impedance detection system simply may not be calibrated properly and therefore may be generating erroneous warning signals even though there is no actual lead fault. Alternatively, the impedance detection system may not be generating warning signals at all—even though a lead fault is present—perhaps because an electrical malfunction causes the detection system to output a constant impedance value regardless of the actual impedance. This is a particularly serious problem as the physician may assume that the pacemaker is working properly even though a permanent lead fault has occurred.

As can he appreciated, it would be highly desirable to provide the physician with more complete information regarding the detected impedance values than merely a warning signal indicating that an unexpected impedance value had been detected of course, some systems may permit the physician to print out or otherwise display diagnostic information pertaining to a lead fault thereby allowing the physician to eventually come to an informed decision about the exact nature of the fault and to determine whether the fault actually exists or not. However, unless such information is provided quickly and efficiently and in a format that allows the physician to immediately determine the nature of the lead fault, it may be of little practical use to the physician, particularly in emergency situations. In general, the more difficult and time-consuming it is for the physician to access lead fault diagnostic information, the less likely he or she will routinely access that information and the less likely he or she will be able to make an informed decision regarding possible lead faults.

Accordingly, it would be desirable to provide an improved system for quickly and efficiently providing useful information to a physician regarding possible lead faults and it is to that end that aspects of the invention are primarily directed.

SUMMARY OF THE INVENTION

In accordance with one aspect of the invention, a real-time impedance monitoring system is provided for use with an implantable medical device having an implantable electrical lead. The impedance monitoring system comprises a means for determining the electrical impedance of the lead as a function of time, with the determination being made substantially in real-time, and a means for graphically displaying the electrical impedance of the lead as a function of time, with the display also being generating substantially in real-time. In one specific example, the implantable medical device is a pacemaker and the impedance monitoring system is within an external programmer device separate from the pacemaker. The means for graphically displaying the impedance of the lead is a computer display screen or a computer printout device.

Hence, a system is provided for graphically displaying the impedance of an electrical lead as it changes in real-time. By providing a graphical display of the impedance in real-time, a physician can easily view the impedance, perhaps in response to a lead fault alarm, to thereby immediately determine the presence and severity of any fault triggering the alarm and to determine whether the fault is permanent or intermittent If intermittent, the physician can easily see whether the intermittent fault lasts only momentarily or for a longer period of time. Additionally, the physician can gain some insight into whether the system is operating correctly. For example, if the time-varying display of impedance reveals a completely constant impedance value that includes no noise or other statistical variations consistent with actual sensed impedance values, the physician may thus suspect that the impedance detection system is malfunctioning. As another example, if the time-varying display reveals impedance values consistent with actual sensed impedance values, but where the impedance values are all either inordinately high or low, the physician may suspect that the impedance detection system is merely miscalibrated. In each case, it is particularly advantageous that the impedance is presented in a graphical form and substantially in real-time to allow the physician to see at a glance the time varying characteristics of the impedance and to thereby be able to make informed decisions promptly and effectively.

Other objects and advantages of the invention are provided as well. Method embodiments of the invention are also provided.

BRIEF DESCRIPTION OF THE DRAWINGS

FIG. 7 is yet another exemplary graphic display, generated by the external programmer of FIG. 2, showing the impedance as a function of time of the electrical leads of the implantable pacemaker of FIG. 1 with values generated from previously recorded data.

DETAILED DESCRIPTION OF THE INVENTION

The invention relates to improved techniques for providing information to a physician regarding the electrical impedance of leads within an implantable medical device. The invention will be described primarily with reference to a pacemaker used in conjunction with an external programmer device, but principles of the invention are applicable to other implantable medical devices or other external devices as well. As such, the examples described herein should not be construed as limiting the scope of the invention.

Figure 1:
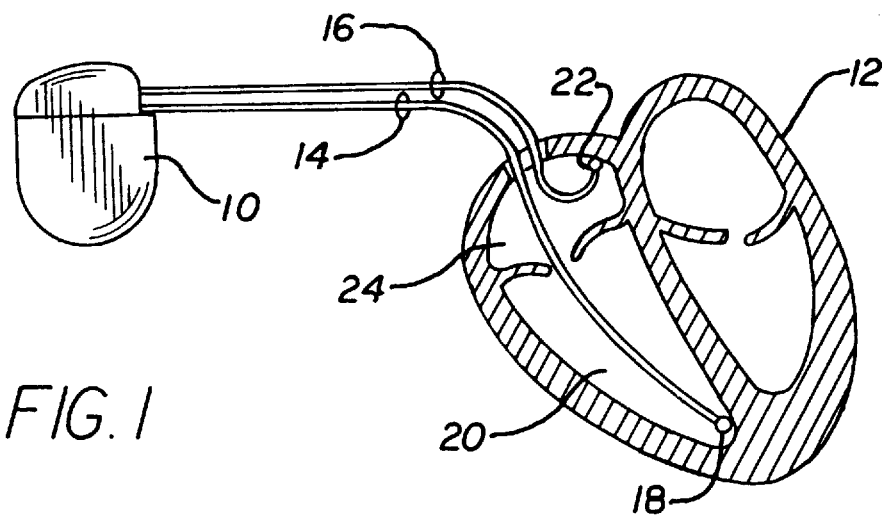
FIG. 1 shows an implantable pacemaker coupled to a heart via a pair of electrical leads.

FIG. 1 illustrates an implantable pacemaker 10 coupled to a heart 12 by way of a ventricular lead 14 and an atrial lead 16. Ventricular lead 14 includes an electrode 18 positioned in the right ventricle 20 of the heart and atrial lead includes an electrode 22 positioned in the right atrium 24 of the heart. Internal components of the pacemaker, to be described in greater detail below, operate to periodically detect electrical characteristics of leads 14 and 16 from which the electrical impedance of the leads can be determined. The detected signals are either transmitted immediately to an external programmer (FIG. 2) or are stored within the pacemaker for subsequent transmission. Pertinent internal components of the pacemaker for detecting, storing and transmitting the electrical characteristics of the leads will be described in greater detail below. Other components of the pacemaker, such as components for monitoring signals received from the heart and for providing responsive therapy, are not directly pertinent to the invention and will not be described in detail herein. Further information regarding internal components of a pacemaker, particularly components directed to efficiently storing and processing data within a pacemaker using "event records, is provided in U.S. Pat. No. 5,431,691 to Snell et al., which is incorporated by reference herein.

Figure 2:
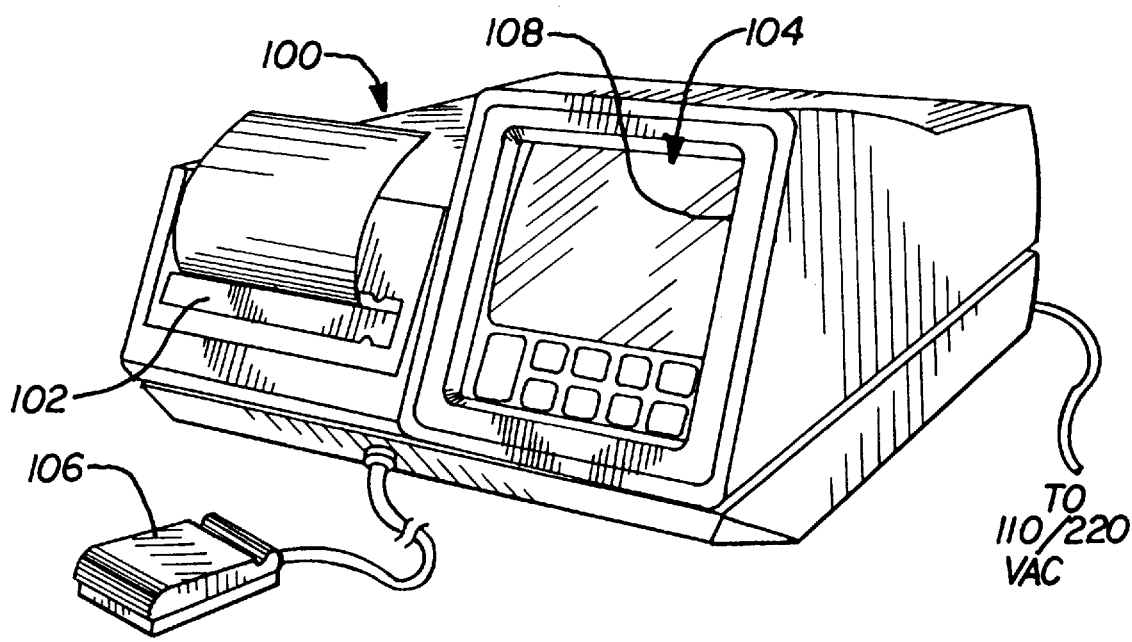
FIG. 2 is a perspective view of an external programmer that may be used for communicating with the implantable pacemaker of FIG. 1.

FIG. 2 illustrates an external programmer 100 configured for receiving the aforementioned electrical signals from pacemaker 10 (FIG. 1), for determining the impedance of the electrical leads of the pacemaker and for generating a time-varying display or printout of the impedance. Programmer 100 includes a printer 102 for printing out a graphical representation of the time-varying impedance and a display screen 104 for displaying a graphical representation of the impedance. Generation of the graphics is subject to the control of a user which may be, for example, a physician or other medical professional. To this end, programmer 100 presents various menus on display screen 104 for use in controlling operation of the programmer both to program pacemaker 10 (FIG. 1) to perform various desired functions and to generate displays on display screen 104 of information received from the pacemaker including the graphical representation of impedance. Programmer 100 receives menu selections from the user through a mouse input device 106 or a touch screen 108 which overlays display screen 104. The presentation of menus to the user via the display screen and the reception and processing of input from the user may be entirely conventional and will not be described in detail. A suitable system for generating menus for use in controlling a pacemaker and for processing data received from the pacemaker, particularly within an "event record" format, is described in the Snell et al. patent referenced above.

Figure 3:
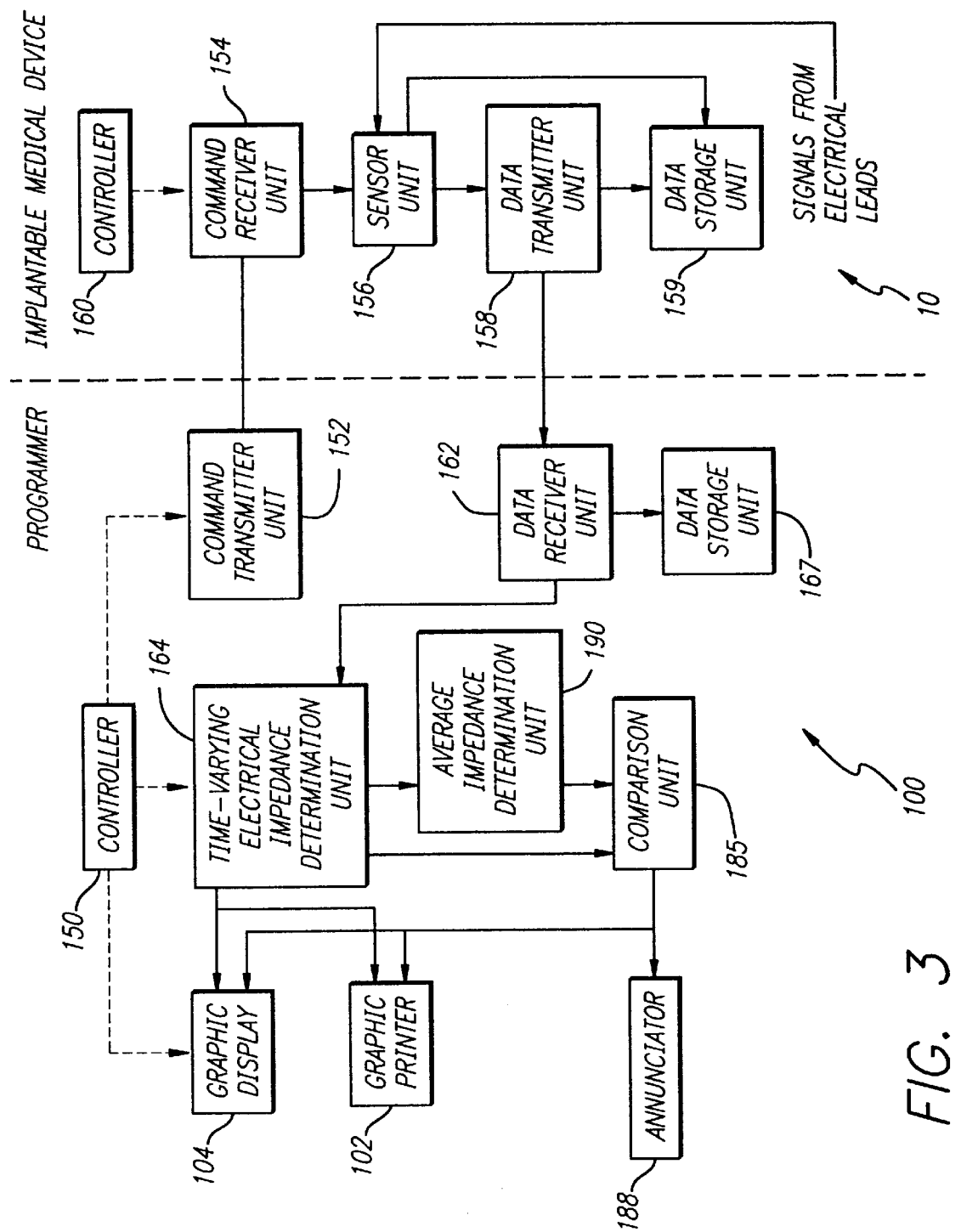
FIG. 3 is block diagram of pertinent components of the implantable pacemaker of FIG. 1 and of the external programmer of FIG. 2 for use in generating and displaying impedance graphics.

With reference to FIG. 3, internal components of pacemaker 10 and programmer 100 that are pertinent to the generation of impedance graphs will now be described. In FIG. 3, components of pacemaker 10 are shown on the right and components of programmer 100 are shown on the left. A controller 150 of programmer 100 controls graphic display 104 to display menus from which a user may select, among other options, for the generation of a real-time display of the impedance of the electrical leads of the pacemaker or the generation of a time-varying display of previously recorded impedance values of the electrical leads. Assuming first that the user chooses a real-time display, perhaps by selecting a menu command entitled MONITOR LEAD IMPEDANCE, controller 150 controls a command transmitter unit 152 of programmer 100 to transmit appropriate command signals to pacemaker 10 causing the pacemaker to begin to detect signals from which the impedance of the ventricular and/or atrial electrical leads 14 and 16 (FIG. 1) and to transmit those values back to the programmer. In one exemplary embodiment, the signals received are representative of pulse amplitude and pulse current values.

Pacemaker 10 receives the commands via a command receiver unit 154 which triggers a sensor unit 156 to receive appropriate electrical signals from the electrical leads from which the impedance can be calculated. The sensed electrical signals are transmitted to the programmer via a data transmission unit 158. Average values of the sensed signals are also periodically stored in a data storage unit 159. In the exemplary embodiment, the sensed signals are averaged over every thirty-two day period throughout the lifetime of the pacemaker. As will be described in greater detail below, the averaged signals are periodically stored in the data storage unit, even while the pacemaker is not actively transmitting the signals to the programmer, as such allows the previously recorded signals to be downloaded and displayed later by the programmer. The operations of all components of pacemaker 10 are under control of a controller 160.

As noted, in the exemplary embodiment, pulse amplitude and pulse current values detected by the pacemaker are employed to calculate impedance. The pulse amplitude and pulse current signals are detected during each pacing cycle. If both atrial and ventricular lead impedance values are monitored simultaneously, the pacemaker alternates during each successive pacing cycle between the atrial lead and the ventricular lead to sense the pulse amplitude and the pulse current. Other suitable techniques for sensing electrical signals from which the impedance of an implantable lead can be calculated are provided in U.S. Pat. No. 4,899,750 to Ekwall and U.S. Pat. No. 5,549,646 to Katz et al., both of which are incorporated by reference herein.

The transmitted electrical signal data is received by programmer 100 via a data receiver unit 162 and is forwarded to a time-varying electrical impedance determination unit 164 which processes the data to calculate the impedance as a function of time. In the embodiment wherein the signals are representative of pulse amplitude and pulse current, impedance determination unit 164 approximates the impedance therefrom using Ohm's law or other related equations. Other suitable techniques for calculating the impedance of an electrical lead are provided in the aforementioned patents to Ekwall and Katz et al. The calculated impedance values are output to graphic display 104 to presentation thereby in graphical form or are output to graphic printer 102, or both. Also, the pulse current and pulse amplitude values received by data receiver unit 162 are stored in a data storage unit 167 for access by other functional units (not shown) of programmer 100 such as units directed to directly displaying the pulse amplitude and pulse current values.

Figure 4:
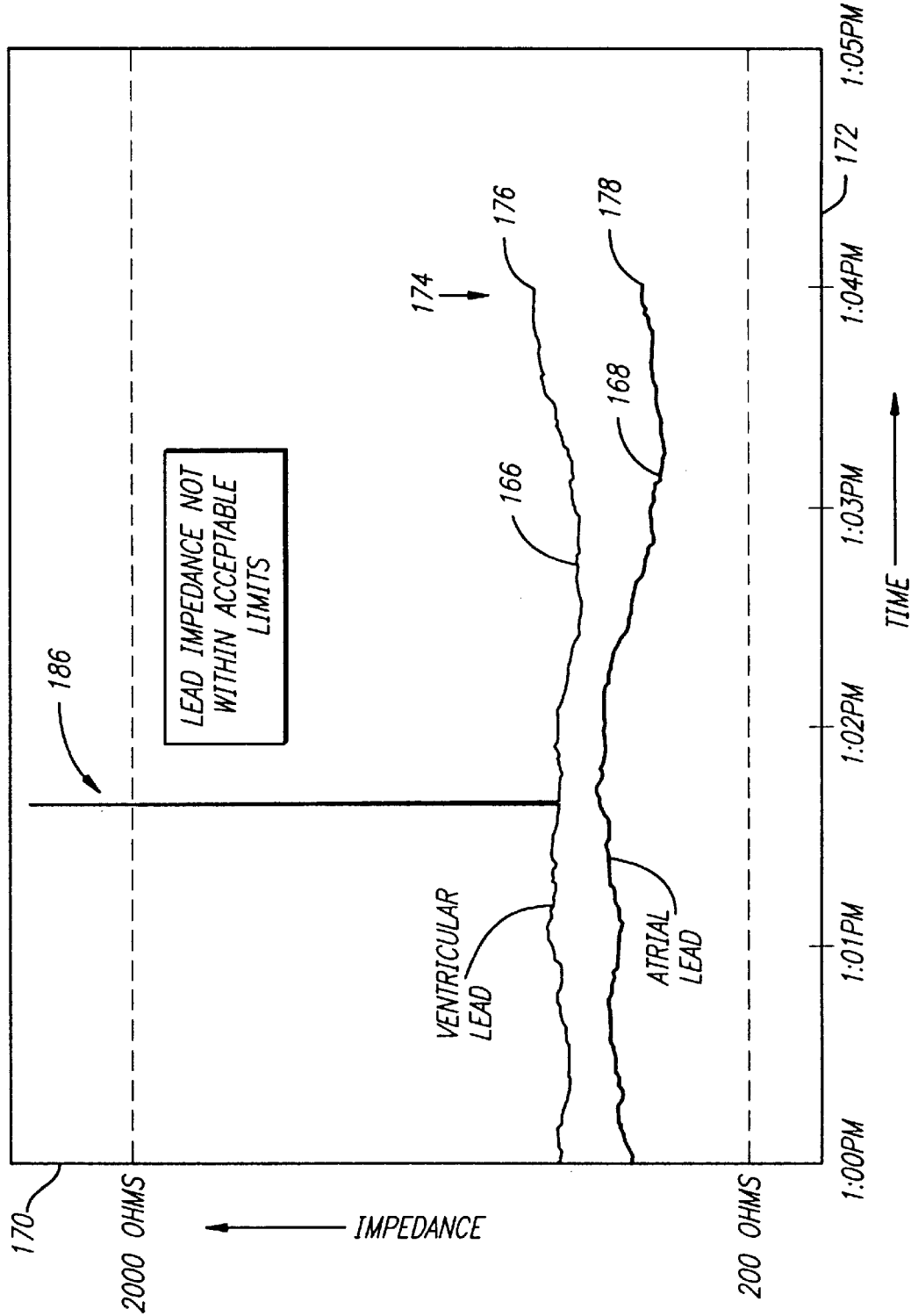
FIG. 4 is an exemplary graphic display, generated by the external programmer of FIG. 2, showing impedance as a function of time for the pair of electrical leads of the implantable pacemaker of FIG. 1 with values presented in real-time and bracketed with predetermined upper and lower boundaries of acceptable impedance.

An exemplary graphical representation of impedance displayed by graphic display 104 or printed out by printer 102 is shown in FIG. 4. More specifically, FIG. 4 illustrates the impedance of the ventricular lead (lead 14 of FIG. 1) with a first line 166 and the impedance of atrial lead (lead 16 of FIG, 1) with a second line 168. Ventricular lead line 166 is thinner than atrial lead line 168 allowing the physician to distinguish the two more easily. The lines may be further distinguished based upon color as well with, for example, the ventricular lead line shown in red, whereas the atrial lead line shown in blue. Appropriate textual annotations are also provided as shown in FIG. 4. Note that some amount of statistical variation occurs in the sensed impedance values representative of normal noise in the system. As will be explained below, if no such noise is present in the impedance graph, such may be indicative of a malfunction in the impedance monitoring system.

The numerical value of the lead impedance is shown along a y-axis 170 along with pre-recorded upper and lower acceptable impedance boundary values of 2000 ohms and 200 ohms, respectively. In other cases, other boundary values may be employed. The current time is displayed along an x-axis 172 of the graph. The current time may be determined from a clock (not shown) provided within the programmer. Alternatively, the pacemaker may transmit the actual time at which the data was sensed (as determined by a clock provided within the pacemaker) along with the sensed data itself to the programmer for use in generating the display of FIG. 4. In either case, the data is presented substantially in real-time so that a physician or other medical professional viewing the display is apprised of the actual impedance of the leads. Although not shown, other graphical information, such as pacing activity or the like, may be simultaneously presented along with impedance by display unit 104 or printer 102. As can be appreciated, a wide variety of useful information can be presented to the physician along with the impedance graphics.

Figure 5:
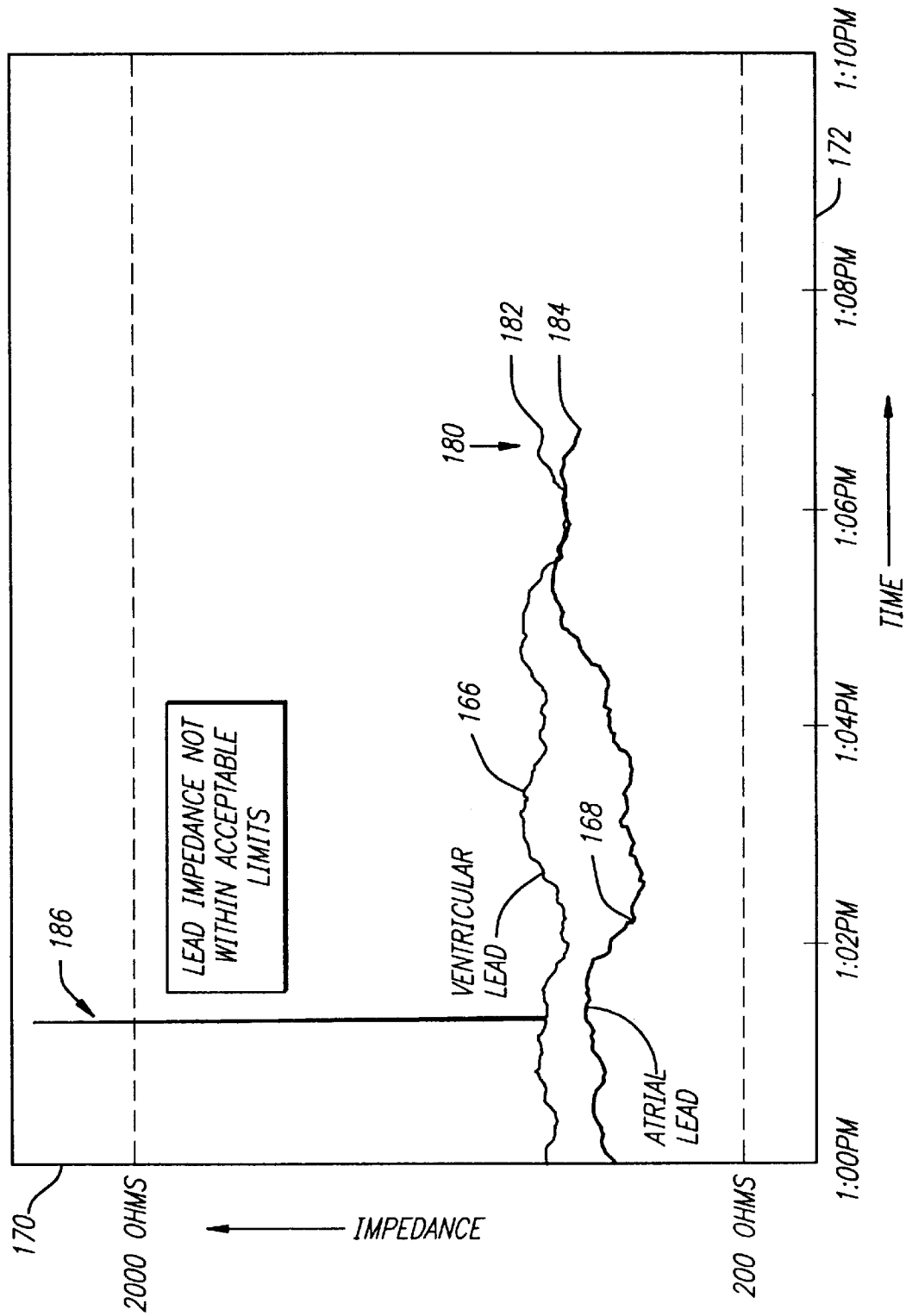
FIG. 5 is another exemplary graphic display, generated by the external programmer of FIG. 2, showing real-time impedance values as in FIG. 4, but re-scaled to cover a longer period of time.

As new impedance values are calculated in real-time, the new values are added to the display yielding a lengthening line of data from left to right beginning at the point in time when the impedance display was initiated and progressing to the current time. In the example of FIG. 4, the impedance display was initiated at 1:00 pm. The current time, as indicated by reference numeral 174, is about 1:04 pm. The most recent data points for the impedance of ventricular and atrial leads, respectively, are points 176 and 178. Eventually, if the physician does not terminate the display of impedance values, the ever-increasing number of impedance values will reach the right-most extremity of the display area. At that time, the programmer automatically re-scales the display to cover a longer period of time. FIG. 5 illustrates a resulting graph wherein the x-axis 172 is re-scaled to cover a ten minutes rather than five minutes. The current time, as indicated by reference numeral 180, is now about 1:08 pm. The most recent data points for the impedance of ventricular and atrial leads, respectively, are points 182 and 184.

Again, eventually the impedance values may reach the right-most extremity of the display area. At that time, programmer begins to scroll the display to the right causing the earliest detected impedance values to be scrolled off of the display or, in other embodiments, the programmer again re-scales the display to cover a still longer period of time. In still other embodiments, the programmer does not re-scale the display at all and instead begins scrolling the display as soon as the impedance values fill the initial time period of, for example, five minutes. As can be appreciated, a wide variety of other alternatives may be exploited as well.

Figure 6:
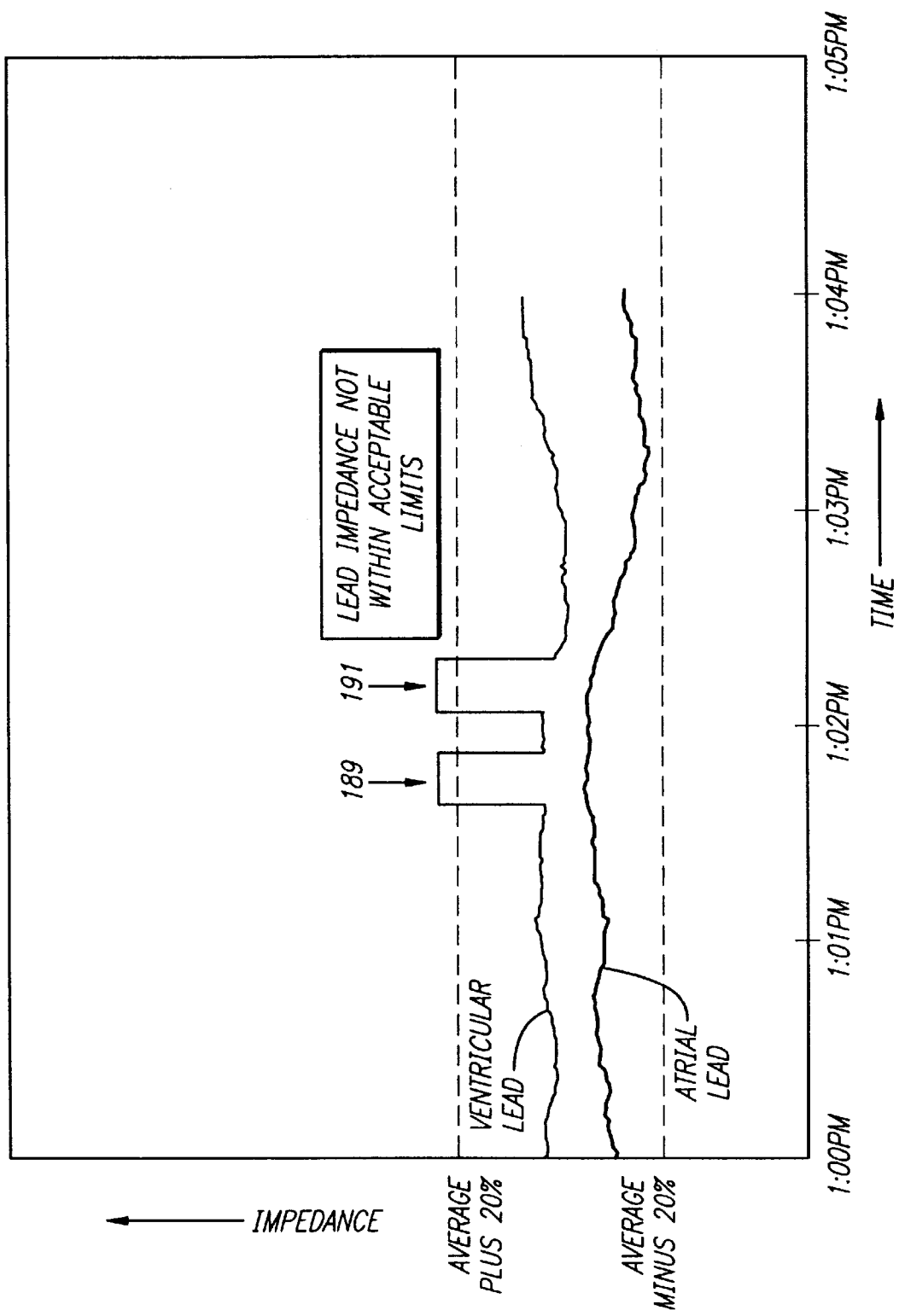
FIG. 6 is yet another exemplary graphic display, generated by the external programmer of FIG. 2, showing the impedance as a function of time of the electrical leads of the implantable pacemaker of FIG. 1 bracketed with variable upper and lower boundaries of acceptable impedance calculated based upon a running average of the impedance rather than upon predetermined boundaries.

As noted in connection with FIG. 4, pre-recorded upper and lower acceptable impedance values are displayed. As impedance determination unit 164 (FIG. 3) calculates each new impedance value, it forwards the new value a comparison unit 185 for comparison with the pre-recorded acceptable boundaries and warning signals are generated if the calculated impedance exceeds the upper boundary or falls below the lower boundary. Such a situation is shown in FIGS. 4 and 5 by the impedance value at point 186 which exceeds the upper boundary of 2000 ohms. Appropriate textual warnings, such as LEAD IMPEDANCE NOT WITHIN ACCEPTABLE LIMITS, are displayed, as shown in FIGS. 5 and 6. Additionally an audio alarm is triggered using an annunciator 188 (FIG. 3).

Eventually, the physician terminates the presentation of impedance graphics by selecting an appropriate menu option, such as a CANCEL MONITOR menu option (not shown), and can thereafter select other programmer operations.

With the combination of the visual display and the audio alarm, a physician operating the programmer is quickly advised of any unusual impedance value indicative of a fault in the lead. The graphic display, in particular, allows the physician to see any rapid change in impedance values representative of an intermittent lead fault in a manner not otherwise easily visualized without a real-time graphic display. Hence, the physician can distinguish at a glance between an intermittent fault and a permanent fault or other permanent malfunction and can take appropriate corrective action.

In use, perhaps during a follow-up appointment with a patient whom just received a pacemaker, the physician controls the programmer to generate the aforementioned real-time impedance display. While watching the display of impedance, the physician vigorously massages the chest of the patient in the vicinity of the pacemaker leads. While watching, one of the main benefits is that the physician does not have to watch continually—just within a few minutes (or seconds). In this manner, the physician can visually determine whether any lead faults occur during the massage. If a lead fault is observed during the massage, then the physician is immediately aware of the fault and can take whatever corrective action is appropriate including, if necessary, replacement of the lead. If no such faults are visible from the display during the massage, the physician can be reasonably assured that the normal motions of the patient will not likely trigger any immediate faults in the lead. (Of course, even if no lead fault is triggered by the vigorous massage, the physician should be aware that a fault may ultimately occur. Hence, the absence of intermittent faults during the massage is no guarantee that no future faults will occur.)

Also, the presentation of a graphic display of impedance allows the physician to more easily determine whether an actual lead fault has occurred rather than some other malfunction. For example, if the graphic display shows a lead impedance that is completely constant and exhibits no noise or other statistical variations representative of the detection of actual impedance values, such may be indicative of malfunction in the programmer or pacemaker rather than an actual fault in the lead itself. Accordingly, the physician may wish to further investigate the possibility of such a malfunction before replacing the leads. As another example, if the graphic display shows a lead impedance that varies significantly on a periodic basis, perhaps exhibiting intermittent faults that occur at precisely timed intervals, such may be indicative of some other type of malfunction in the programmer or pacemaker rather than an actual fault in the lead. As can be appreciated, a wide range of anomalous characteristics to the time-varying impedance display may be presented as a result of some type of equipment malfunction. In general, any such characteristic that is not representative of normal variations in actual sensed impedance values and also not representative of an actual lead fault is likely indicative of an malfunction in the pacemaker or the programmer and appropriate corrective action should be taken.

The ability to view the time-varying impedance values is particularly helpful in situations where a fault has occurred in the lead or a malfunction has occurred in the impedance monitoring system but where the impedance values remain within the predetermined acceptable boundaries. For example, the display may reveal sharp intermittent fluctuations in impedance indicative of a partial lead fault but where the impedance never exceeds the predetermined boundaries. Since the impedance values remain within the acceptable boundaries, no audible or visual alarm would otherwise be presented and the physician might otherwise conclude that the system is working properly. However, by providing a time-varying display of the impedance, the physician can see at a glance that anomalous behavior is occurring and can take appropriate action.

Thus the time-varying impedance display allows the physician or other medical professional operating the programmer to gain considerable insight into the exact nature of a lead fault, if any, and into whether the impedance monitoring system is functioning properly. As can be appreciated, in systems of the prior art which provide only an audible or visual warning of an unexpected impedance value, the physician may not be able to make prompt and informed decisions regarding the integrity of the leads or of the impedance monitoring system and therefore may not be able to make a prompt and correct diagnosis of the patient ailments.

As noted, FIGS. 4 and 5 illustrate any exemplary display wherein the predetermined upper and lower acceptable impedance boundary values are displayed. Alternatively, the programmer may calculate upper and lower boundaries based upon a running average value of the sensed impedance. FIG. 6 illustrates an exemplary graphic display of impedance similar to that of FIG. 4 but wherein an upper boundary equal to the average impedance plus 20% is displayed along with a lower boundary equal to the average impedance minus 20%. (The drawing of FIG. 6 is not necessarily to scale.) To generate the display of FIG. 6, programmer 100 of FIG. 3 includes an average impedance determination unit 190 which calculates a running average based upon, for example, the last few minutes worth of impedance values. Comparison unit 185 compares the current impedance to the running average and triggers audible and visual warnings if the current impedance falls outside the upper and lower boundaries. Such allows a sharp change in impedance to trigger a warning even if though the change may not be sufficient to cause the impedance to exceed a predetermined fixed lower or upper limit (such as 200 ohms and 2000 ohms, respectively). As such, partial faults in the lead, which do not cause a radical change in impedance, are nevertheless detected and an audible and visual warning is generated. In the example of FIG. 6, partial faults 189 and 191 cause the impedance of the ventricular lead to exceed the upper 20% threshold.

The duration over which the running average is maintained may be pre-programmed to any desired amount by the manufacturer or, in other cases, by the user of programmer 100. Alternatively, the programmer may merely be programmed to calculate the average based upon all impedance values calculated during a particular impedance monitoring session. In still other embodiments, the pacemaker itself may track the average lead impedance and forward that average value to the programmer for use by comparison unit 185. The average maintained by the pacemaker may be, for example, a running average over a predetermined period of time or perhaps an average taken over the whole lifetime of the pacemaker. In still other embodiments, warnings may be generated based upon either a variation from predetermined fixed boundaries or a variation from running average-based boundaries. A wide range of alternatives may be implemented for triggering warnings consistent with the general principles of the invention.

What has been described thus far are operations of the pacemaker 10 and programmer 100 of FIGS. 1 and 2, respectively, for generating real-time displays. Additionally, the programmer may be controlled to display a non-real-time graphical representation of the impedance of the leads of the pacemaker over the whole lifetime of the pacemaker. As noted above in connection with FIG. 3, the pacemaker includes a data storage unit 159 which periodically stores a thirty-two day average of the electrical signals from which the impedance of the atrial and ventricular leads can be calculated, i.e. the data storage unit stores average pulse amplitude and pulse current values.

To access the stored data, controller 150 of programmer 100 presents menus on display 104 allowing the physician to select generation of a historical, i.e. non-real-time, display of impedance values. Controller 150 causes command transmitter unit 152 to transmit an appropriate command to the command receiver unit 154 of the pacemaker causing the prerecorded thirty-two day averages of the sensed data to be retrieved from data storage unit 159 and transmitted back to the programmer using data transmitter unit 158. Programmer 100 then proceeds substantially as previously described to calculate the impedance therefrom and to display or printout graphical representations of the impedance calculated from the data. In other embodiments, data storage unit 159 of the pacemaker stores calculated average impedance values rather than averages of the pulse amplitude and pulse current values.

Whereas the real-time displays are scaled over a period of five or ten minutes, the historical displays are scaled over periods of months or years. To this end, the programmer determines the implantation date of the pacemaker and the current date. The implantation date may be determined by interrogating the pacemaker, perhaps while also accessing the prerecorded data from data storage unit 158. If the pacemaker has not been implanted for at least thirty-two days, no graph is displayed. Rather, a message is displayed indicating that the pacemaker has not been implanted long enough to generate the historical display. If the pacemaker had been implanted for at least thirty-two days but less than one year, an impedance display is generated with an x-axis (time axis) scaled from zero to twelve months. If the pacemaker had been implanted between one and two years previously, the display is scaled from zero to twenty-four months. If the pacemaker had been implanted between two and five years previously, the display is scaled from zero to five years. If the pacemaker had been implanted between five and ten years previously, the display is scaled from zero to ten years Data beyond ten years is either ignored or the display is re-scaled yet again.

FIG. 7 illustrates an exemplary display of an historical impedance graph scaled between zero and twenty-four months (and smoothed with an appropriate smoothing algorithm). As can be seen, both the implantation date and the current date (i.e. the interrogation date) are shown in the graph by vertical lines. Also, in contrast to the example of FIGS. 4 which shows a single intermittent lead fault that lasts only a few seconds, the example of FIG. 5 reveals several intermittent lead faults 190, 192 and 194 each lasting for at least several weeks.

Thus, in addition to providing real-time displays of current impedance values, the exemplary system described herein also displays the historical trend in impedance over the entire lifetime of the pacemaker allowing the physician to gain further insight into the impedance characteristics, and therefore the integrity, of the electrical leads of the pacemaker. In one embodiment, the historical display is generated first upon selection of a lead impedance display function, then the aforementioned real-time displays are generated only if the user specifically specifies that the lead impedance be monitored.

What has been described are systems for displaying time-varying graphs of impedance. The various functional components of the exemplary system may be implemented using any appropriate technology including, for example, microprocessors running software programs or application specific integrated circuits (ASIC'S) executing hard-wired logic operations.

What is claimed is:

1. In an implantable stimulation system of the type having an implantable lead for delivering stimulation pulses and means for determining an electrical impedance of the lead, an improved system for detecting faults in the implantable lead, the improvement comprising:

means for determining the electrical impedance of the lead as a function of time, the determination being made substantially in real-time; and means for graphically displaying the electrical impedance of the lead as a function of time, the display being generated substantially in real-time;

whereby intermittent faults, when present, are graphically displayed in real-time.

2. The system of claim 1, wherein the means for determining the electrical impedance of the lead comprises:

means for receiving pulse amplitude and pulse current data from the pacemaker, both as a function of time, and means for calculating the electrical impedance therefrom.

3. The system of claim 1, wherein the means for graphically displaying the impedance of the lead comprises a computer display screen.

4. The system of claim 1, wherein the means for graphically displaying the impedance of the lead comprises a computer printout device.

5. The system of claim 1, further comprising:
   means for receiving previously recorded data from the implantable stimulation system wherein the data is representative of changes in electrical characteristics of the lead as a function of time;
   means for determining the electrical impedance of the lead as a function of time from the previously recorded electrical characteristics; and
   means for graphically displaying the electrical impedance of the lead as a function of time.

6. The system of claim 1, wherein the means for graphically displaying comprises:
   means for displaying a time parameter along an x-axis of a display device; and
   means for displaying the electrical impedance along a y-axis of the display device.

7. The system of claim 6, wherein the means for graphically displaying further comprises:
   means for displaying the time parameter within a first time scale for a initial period of time; and
   means for displaying the time parameter re-scaled within a second time scale for time periods exceeding the initial period of time.

8. The system of claim 1, further comprising:
   means for defining upper and lower impedance limits; and
   warning means for providing a warning signal when the electrical impedance exceeds the impedance limits.

9. The system of claim 8, wherein the upper and lower impedance limits are 2000 ohms and 200 ohms, respectively.

10. The system of claim 8, wherein the warning means comprises means for generating an audible alarm signal.

11. The system of claim 8, wherein the warning means comprises means for displaying a textual warning.

12. The system of claim 8, wherein the warning means comprises:
    means for displaying a graphical icon adjacent to any impedance value exceeding the impedance limits.

13. The system of claim 8, further comprising:
    means for determining the average electrical impedance of the lead over a period of time; and
    wherein the warning means comprises means for generating an alarm signal whenever the electrical impedance varies from the average electrical impedance by more than a predetermined amount.

14. The system of claim 8, wherein the predetermined amount is twenty percent.

15. In an implantable stimulation system of the type having a first and second implantable lead for delivering stimulation pulses to the atrium and the ventricle, respectively, and means for determining an electrical impedance of each lead, an improved system for detecting faults in the implantable leads, the improvement comprising:
    means for separately determining the electrical impedance of each lead as a function of time, the determination being made substantially in real-time; and
    means for graphically displaying the electrical impedance of each lead as a function of time, the display being generating substantially in real-time, the impedance of the first lead being displayed separately;
    whereby intermittent faults, when present, are graphically displayed is real-time.

16. The system of claim 15, wherein the means for graphically displaying comprises:
    means for displaying different colors; and
    wherein the impedance of the first lead is displayed using a first color and the impedance of the second lead is displayed using a second color.

17. The system of claim 15, wherein the means for graphically displaying comprises:
    means for displaying lines of different thickness; and
    wherein the impedance of the first lead is displayed using a first line thickness and the impedance of the second lead is displayed using a second line thickness.

18. An impedance monitoring system for use with an implantable stimulation device having an implantable electrical lead connected thereto, the impedance monitoring system comprising:
    an electrical impedance measuring circuit, located within the stimulation device and coupled to the lead, which measures the electrical voltage and current delivered by the lead as a function of time, the determination being made substantially in real-time; and
    an external processing system, telemetrically coupled to the stimulation device, having a processor that calculates lead impedance based on the measured voltage and current received from the stimulation device, the external display device further including a display unit which graphically displays the electrical impedance of the lead as a function of time, the display being generated substantially in real-time;
    whereby intermittent faults, when present, are graphically displayed in real-time.

19. A method for detecting electrical faults in an implantable electrical lead, the method comprising the steps of:
    determining a plurality of electrical lead impedance values over a period of time; and
    graphically displaying the electrical lead impedance as a function of time, the display being generated substantially in real-time;
    whereby intermittent faults, when present, are graphically identifiable.

20. The method for detecting electrical faults as recited in claim 19, further comprising the steps of:
    defining upper and lower impedance limits; and
    providing a warning signal when the electrical impedance exceeds the impedance limits.

* * * * *